United States Patent
Robichaud et al.

(10) Patent No.: US 11,622,801 B2
(45) Date of Patent: Apr. 11, 2023

(54) PATIENT-SPECIFIC FIXATION PLATE WITH WEDGE MEMBER FOR KNEE OSTEOTOMIES

(71) Applicant: LABORATOIRES BODYCAD INC., Québec (CA)

(72) Inventors: Jean Robichaud, St-Aubert (CA); Hugo Robichaud, Quebec (CA); Jonathan Laflamme, Quebec (CA)

(73) Assignee: LABORATOIRES BODYCAD INC., Québec (CA)

( * ) Notice: Subject to any disclaimer, the term of this patent is extended or adjusted under 35 U.S.C. 154(b) by 412 days.

(21) Appl. No.: 16/609,969

(22) PCT Filed: Aug. 22, 2019

(86) PCT No.: PCT/CA2019/051151
§ 371 (c)(1),
(2) Date: Oct. 31, 2019

(87) PCT Pub. No.: WO2020/037421
PCT Pub. Date: Feb. 27, 2020

(65) Prior Publication Data
US 2021/0401476 A1    Dec. 30, 2021

Related U.S. Application Data

(60) Provisional application No. 62/722,403, filed on Aug. 24, 2018, provisional application No. 62/722,424, filed on Aug. 24, 2018.

(51) Int. Cl.
*A61B 17/80* (2006.01)
*A61B 34/10* (2016.01)
*A61B 17/56* (2006.01)

(52) U.S. Cl.
CPC .......... *A61B 17/8095* (2013.01); *A61B 34/10* (2016.02); *A61B 2017/568* (2013.01); *A61B 2034/105* (2016.02); *A61B 2034/108* (2016.02)

(58) Field of Classification Search
CPC .................................................. A61B 17/8095
See application file for complete search history.

(56) References Cited

U.S. PATENT DOCUMENTS

| 2,002,021 A | 5/1935 | Rouse |
| 5,620,448 A | 4/1997 | Puddu |

(Continued)

FOREIGN PATENT DOCUMENTS

| CN | 103393459 A | 11/2013 |
| CN | 207721848 U | 8/2018 |
| WO | WO-2015/003284 A2 | 1/2015 |

OTHER PUBLICATIONS

Azernikov S. (2013) Inhomogeneous Axial Deformation for Orthopedic Surgery Planning. In: Csurka G., Kraus M., Mestetskiy L., Richard P., Braz J. (eds) Computer Vision, Imaging and Computer Graphics. Theory and Applications. VISIGRAPP 2011. Communications in Computer and Information Science, vol. 274, p. 69-85. Springer, Berlin, Heidelberg.

(Continued)

*Primary Examiner* — Samuel S Hanna
(74) *Attorney, Agent, or Firm* — Marshall, Gerstein & Borun LLP

(57) ABSTRACT

A fixation plate for securing an opening formed in a bone is provided. The fixation plate includes: a body securable to the bone, the body having a bone interface side and an outward facing side; and a wedge element extending from the bone interface side of the body for inserting into the opening formed in the bone. The wedge element is shaped to conform to contours of the opening formed in the bone. In some embodiments, the wedge element is provided with an evo- (Continued)

lutive canal. A corresponding method for designing a patient-specific fixation plate is also provided.

11 Claims, 9 Drawing Sheets

(56) References Cited

U.S. PATENT DOCUMENTS

| | | | |
|---|---|---|---|
| 5,749,875 A | 5/1998 | Puddu | |
| 6,017,342 A | 1/2000 | Rinner | |
| 6,066,142 A | 5/2000 | Serbousek et al. | |
| 6,461,359 B1 | 10/2002 | Tribus et al. | |
| 7,794,467 B2 | 9/2010 | McGinley et al. | |
| 7,935,119 B2 | 5/2011 | Ammann et al. | |
| 8,083,746 B2 | 12/2011 | Novak | |
| 8,092,465 B2 | 1/2012 | Metzger et al. | |
| 8,137,406 B2 | 3/2012 | Novak et al. | |
| 8,211,112 B2 | 7/2012 | Novak et al. | |
| 8,241,292 B2 | 8/2012 | Collazo | |
| 8,241,293 B2 | 8/2012 | Stone et al. | |
| 8,337,507 B2 | 12/2012 | Lang et al. | |
| 8,388,690 B2 | 3/2013 | Singhatat et al. | |
| 8,409,209 B2 | 4/2013 | Ammann et al. | |
| 8,484,001 B2 | 7/2013 | Glozman et al. | |
| 8,594,395 B2 | 11/2013 | Roose et al. | |
| 8,632,547 B2 | 1/2014 | Maxson et al. | |
| 8,709,052 B2 | 4/2014 | Ammann et al. | |
| 8,753,348 B2 | 6/2014 | DiDomenico et al. | |
| 8,828,087 B2 | 9/2014 | Stone et al. | |
| 8,979,866 B2 | 3/2015 | Patel et al. | |
| 8,998,903 B2 | 4/2015 | Price et al. | |
| 9,014,835 B2 | 4/2015 | Azernikov et al. | |
| 9,072,555 B2 | 7/2015 | Michel | |
| 9,456,833 B2 | 10/2016 | Maxson et al. | |
| 9,480,490 B2 | 11/2016 | Metzger et al. | |
| 9,486,228 B2 | 11/2016 | Saw et al. | |
| 9,603,605 B2 | 3/2017 | Collazo | |
| 9,687,261 B2 | 6/2017 | Serbousek et al. | |
| 9,707,023 B2 | 7/2017 | Ammann et al. | |
| 9,770,302 B2 | 9/2017 | Kang et al. | |
| 9,814,533 B2 | 11/2017 | Park et al. | |
| 9,833,245 B2 | 12/2017 | Maxson | |
| 9,877,758 B2 | 1/2018 | Michel | |
| 9,877,790 B2 | 1/2018 | Bojarski et al. | |
| 9,943,348 B2 | 4/2018 | Schelling | |
| 10,245,089 B2 | 4/2019 | Paik | |
| 2005/0209599 A1 | 9/2005 | Brunsvold | |
| 2006/0052795 A1 | 3/2006 | White | |
| 2007/0191848 A1 | 8/2007 | Wack et al. | |
| 2009/0082816 A1 | 3/2009 | Graham et al. | |
| 2011/0213376 A1* | 9/2011 | Maxson | A61B 17/1764 606/88 |
| 2013/0338673 A1 | 12/2013 | Keppler | |
| 2015/0051650 A1 | 2/2015 | Verstreken et al. | |
| 2015/0305752 A1 | 10/2015 | Eash | |
| 2016/0095634 A1 | 4/2016 | Meyer | |
| 2016/0113784 A1 | 4/2016 | Robichaud | |
| 2016/0192949 A1 | 7/2016 | Robichaud et al. | |
| 2016/0235454 A1 | 8/2016 | Treace et al. | |
| 2017/0035479 A1* | 2/2017 | Paik | A61B 17/8061 |
| 2017/0325823 A1 | 11/2017 | Phillips-Hungerford et al. | |
| 2017/0325826 A1 | 11/2017 | Bake et al. | |

OTHER PUBLICATIONS

Azernikov et al., "Inhomogeneous Axial Deformation for Orthopedic Surgery Planning," Communications in Computer and Information Science, 274:69-85 (2013).
International Search Report and Written Opinion for Application No. PCT/CA2019/051147, dated Oct. 15, 2019.
International Search Report and Written Opinion for Application No. PCT/CA2019/051148, dated Oct. 24, 2019.
International Search Report and Written Opinion for Application No. PCT/CA2019/051149, dated Oct. 7, 2019.
International Search Report and Written Opinion for Application No. PCT/CA2019/051151, dated Oct. 22, 2019.
International Search Report and Written Opinion for Application No. PCT/CA2019/051153, dated Sep. 25, 2019.
International Search Report and Written Opinion for Application No. PCT/CA2019/051156, dated Sep. 30, 2019.
International Search Report and Written Opinion for Application No. PCT/CA2019/051157, dated Oct. 25, 2019.

* cited by examiner

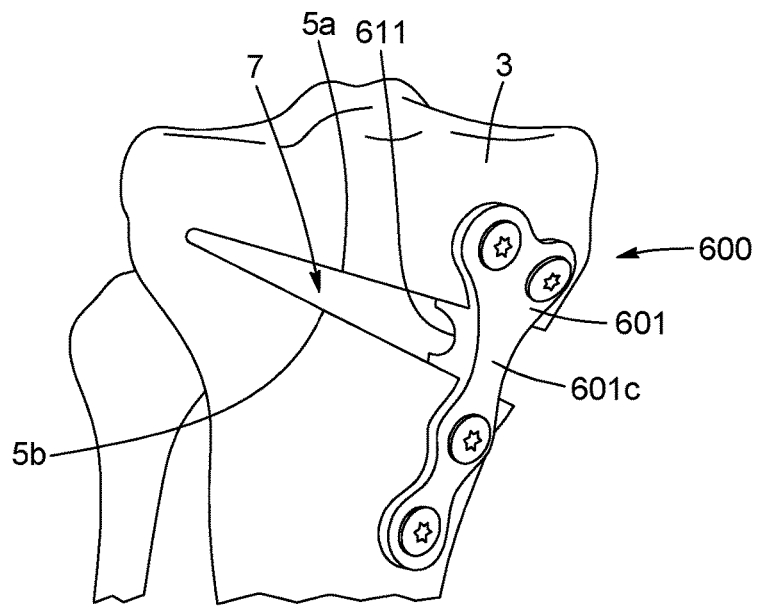
FIG. 2
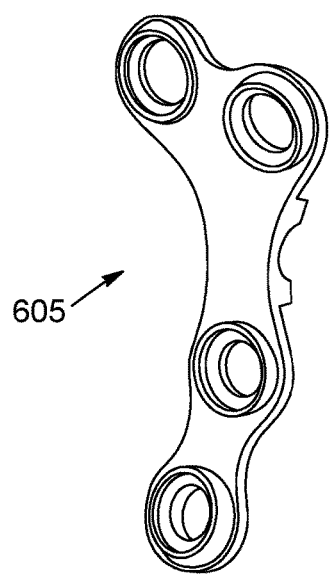 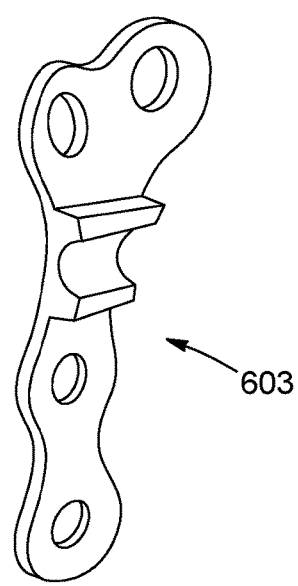 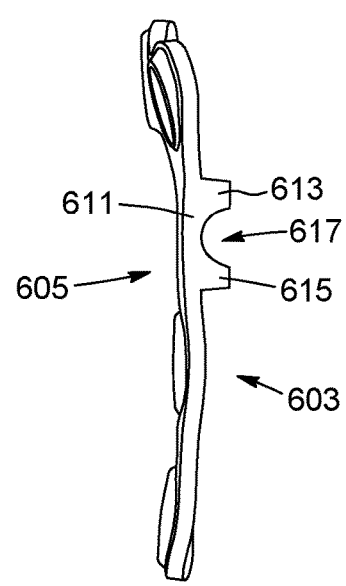
FIG. 2A  FIG. 2B  FIG. 2C

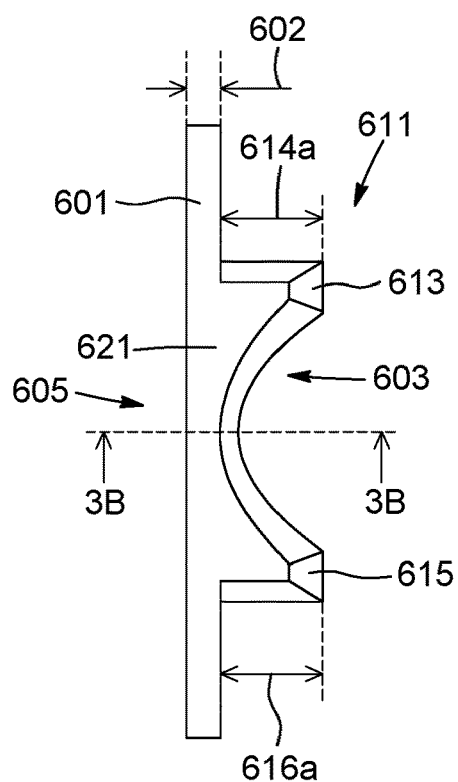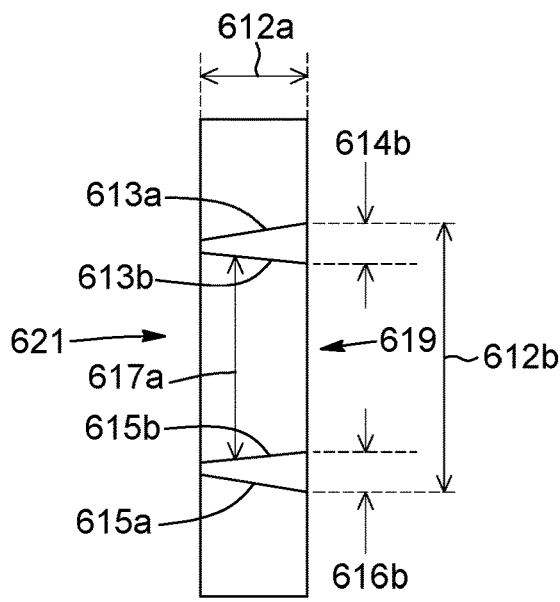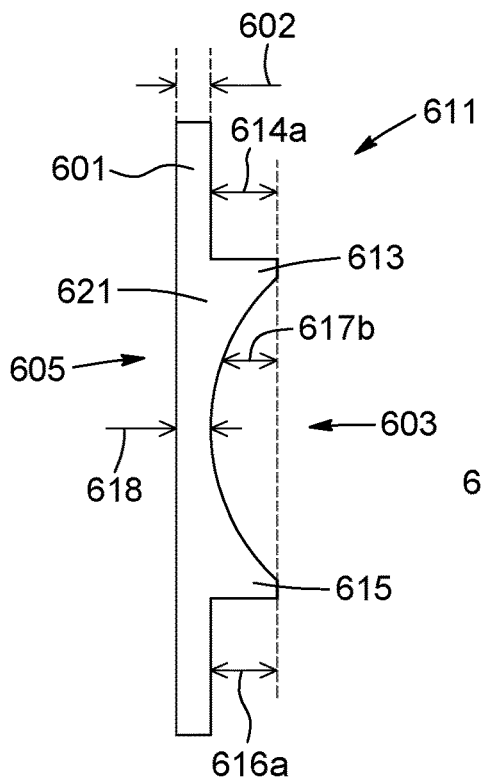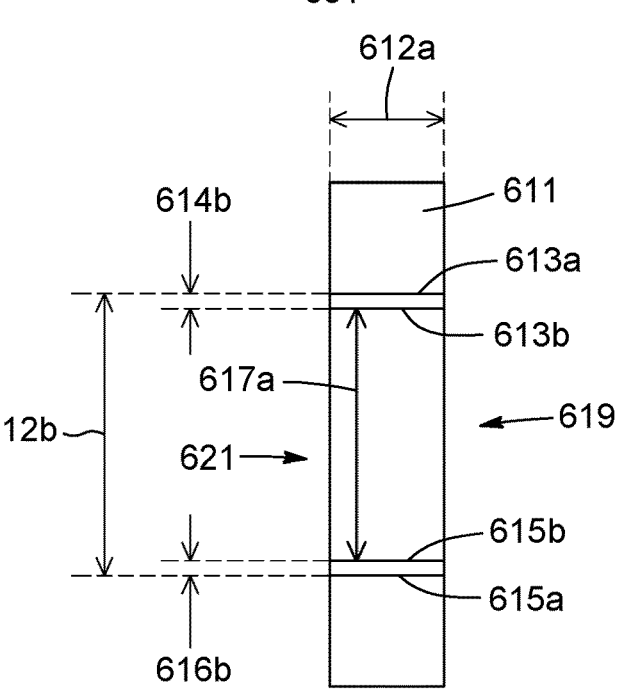
FIG. 3
FIG. 3A
FIG. 3B
FIG. 4
FIG. 4A

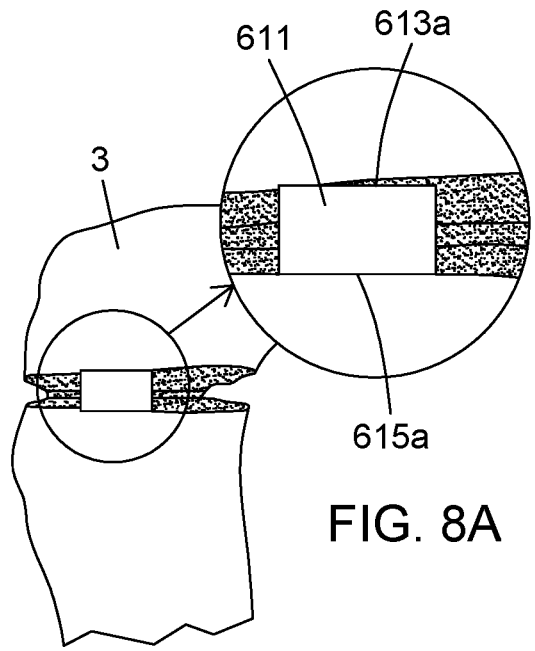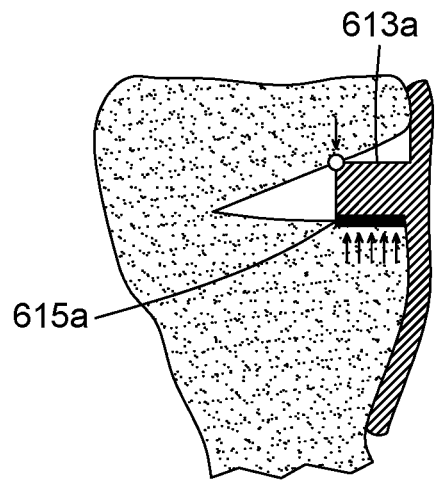
FIG. 8  FIG. 8A  FIG. 8B
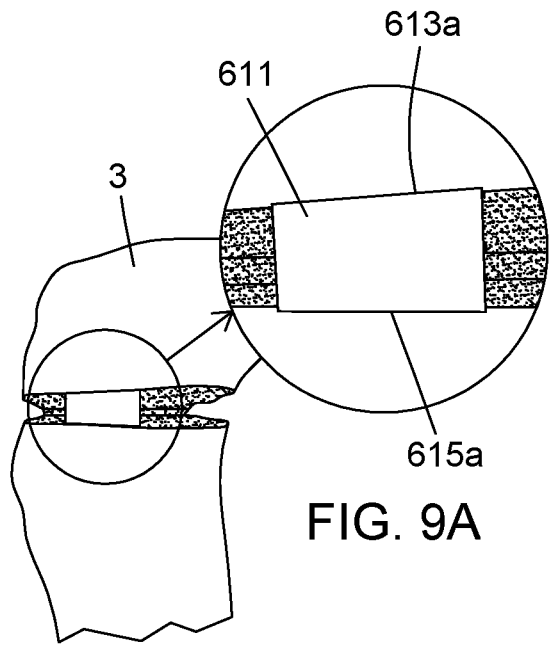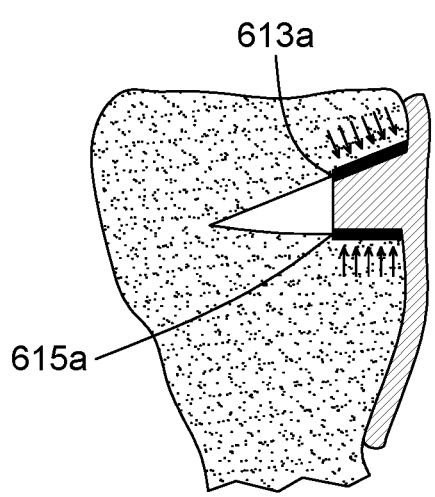
FIG. 9  FIG. 9A  FIG. 9B

PATIENT-SPECIFIC FIXATION PLATE WITH WEDGE MEMBER FOR KNEE OSTEOTOMIES

RELATED APPLICATIONS

This application claims the benefit of U.S. Provisional Application No. 62/722,424, filed Aug. 24, 2018, entitled "PATIENT-SPECIFIC FIXATION PLATE WITH WEDGE MEMBER FOR KNEE OSTEOTOMIES", and of U.S. Provisional Application No. 62/722,403, filed Aug. 24, 2018, entitled "SURGICAL KIT FOR KNEE OSTEOTOMIES AND CORRESPONDING PREOPERATIVE PLANNING METHOD", the entirety of which are incorporated herein by reference.

TECHNICAL FIELD

The technical field generally relates to tools used in knee osteotomy procedures, and more particularly in high tibial osteotomies.

BACKGROUND

Knee osteotomies are orthopedic procedures which aim to correct the alignment of knee joints to adjust pressure distribution. A high tibial osteotomy is a type of knee osteotomy which involves correcting the alignment of a knee joint by reconfiguring the mechanical axis of the tibia. Depending on the required correction angle, the high tibial osteotomy can be an open wedge osteotomy or a closed wedge osteotomy. In an open wedge osteotomy, a planar cut is made in the tibia below the knee, and the tibia bone is opened along the planar cut to form a wedge-shaped opening with a specified angle. In a closed wedge osteotomy, a wedge of bone having a specified angle is removed from the tibia bone below the knee, and the tibia bone is closed along the wedge. After the bone is opened or closed, it is retained in place by installing a fixation plate. The opening or closing effectively adjusts the angle of the tibia relative to the femur, thereby reconfiguring how pressure between the tibia and the femur is distributed in the knee.

Existing tools and procedures are limited in the accuracy and precision with which the alignment of the knee can be corrected. There is therefore much room for improvement.

SUMMARY

According to an aspect, a fixation plate for securing an opening formed in a bone is provided. The fixation plate includes: a body securable to the bone, the body having a bone interface side and an outward facing side; and a wedge element extending from the bone interface side of the body for inserting into the opening formed in the bone; wherein the wedge element is shaped to conform to contours of the opening formed in the bone.

According to an aspect, a fixation plate for securing an opening formed in a bone is provided. The fixation plate includes: a body securable to the bone, the body having a bone interface side and an outward facing side; and a wedge element extending from the bone interface side of the body for inserting into the opening formed in the bone; wherein the wedge element comprises a proximal abutment for abutting against a proximal internal surface of the bone in the opening, and a distal abutment for abutting against a distal internal surface of the bone in the opening, said proximal and distal abutments being spaced apart from one another via a canal.

According to an aspect, a method for designing a patient-specific fixation plate is provided. The method includes the steps of: a) obtaining 3D model of the patient's bone; b) determining an expected shape of an opening to be formed in the patient's bone using the 3D model; c) designing a fixation plate having a body and a wedge element extending therefrom, and configuring the wedge element to conform to the expected shape of the opening; and d) manufacturing the fixation plate according to the design.

BRIEF DESCRIPTION OF THE DRAWINGS

FIG. 2 is a perspective view of a fixation plate securing an open wedge formed in a patient's tibia bone, according to an embodiment in which the fixation plate is provided with a wedge element; FIGS. 2A, 2B and 2C are respectively front perspective, rear perspective and side views of the fixation plate of FIG. 2.

FIG. 3 is a side view of a portion of a fixation plate having a wedge element with an evolutive canal and patient-specific bone conforming surfaces, according to an embodiment; FIG. 3A is a rear view of the fixation plate of FIG. 3; and FIG. 3B is a cross sectional view of the fixation plate of FIG. 3 taken along line 3B-3B.

FIG. 4 is a side view of section of a fixation plate having a straight wedge element, according to an embodiment; FIG. 4A is a rear view thereof.

FIG. 8 is a perspective view showing an open wedge formed in a patient's tibia bone supported by a straight wedge, according to an embodiment; FIG. 8A is a detail view of the wedge of FIG. 8; FIG. 8B is a partial cross section of the bone and wedge of FIG. 8, showing stress distribution at an interface between the wedge and the bone.

FIG. 9 is a perspective view showing an open wedge formed in a patient's tibia bone supported by a patient-specific, bone conforming wedge, according to an embodiment; FIG. 9A is a detail view of the wedge of FIG. 9; FIG. 9B is a partial cross section of the bone and wedge of FIG. 9, showing stress distribution at an interface between the wedge and the bone.

DETAILED DESCRIPTION

Figure 1A:
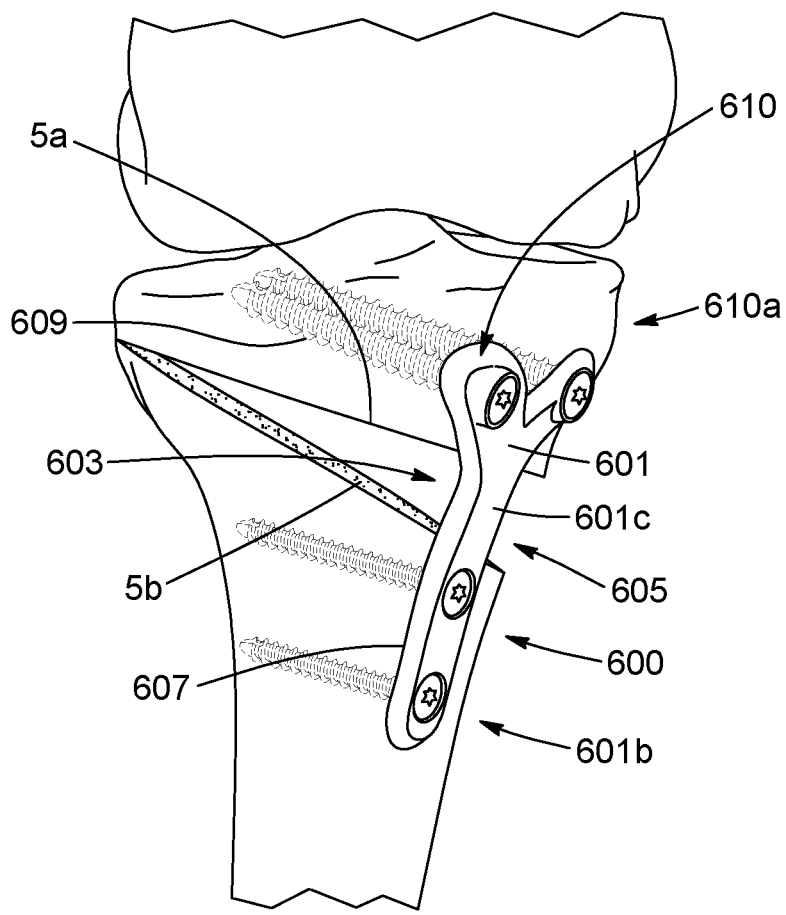
FIG. 1A is a perspective view of a fixation plate securing an open wedge formed in the patient's tibia bone, according to an embodiment.
Figure 1B:
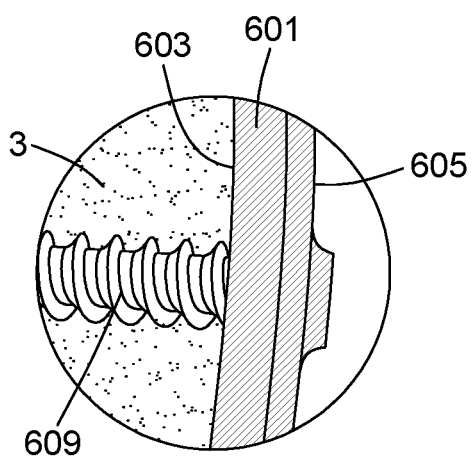
FIG. 1B is a partial-cross section detail view of the fixation plate secured directly to the patient's tibia bone via a fastener.
Figure 5:
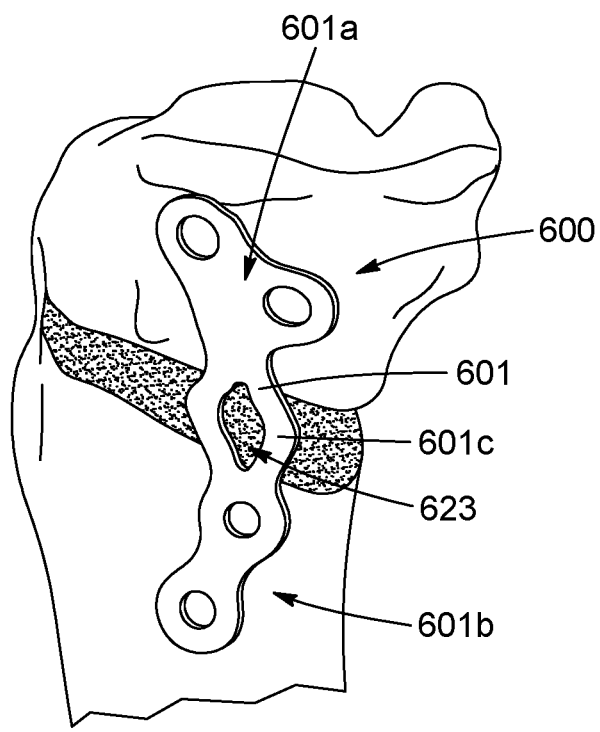
FIG. 5 is a perspective view of a fixation plate securing an open wedge formed in a patient's tibia bone, according to an embodiment in which the fixation plate is provided with two wedge elements.
Figure 5A:
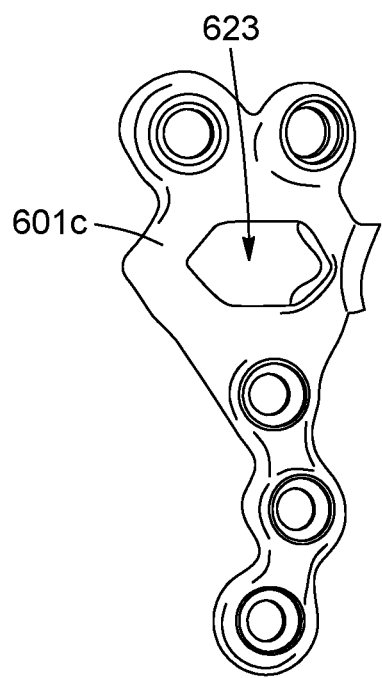
FIGS. 5A and 5B are respective front and rear views of the fixation plate of FIG. 5.
Figure 5B:
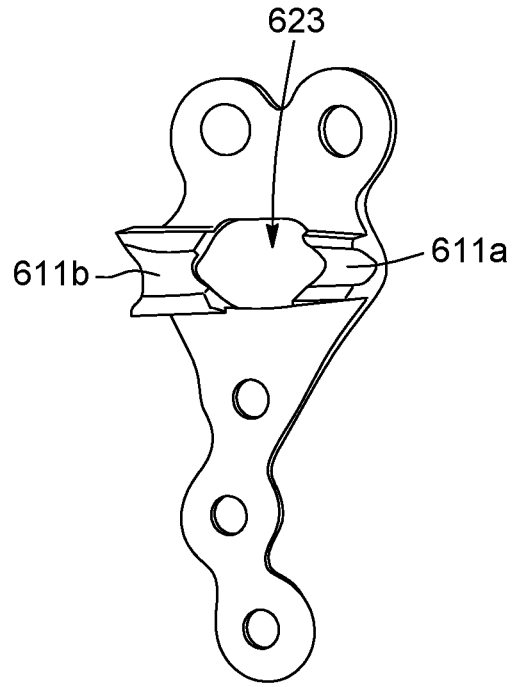
Figure 6A:
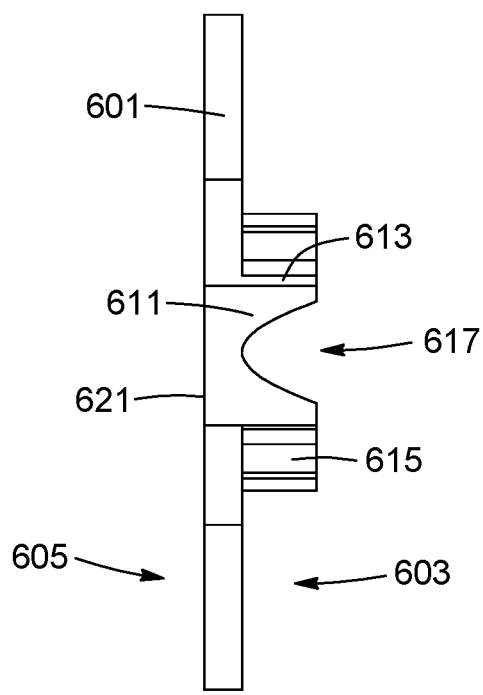
FIG. 6A is a side view of a portion of a fixation plate having two wedge elements, according to an embodiment.
Figure 6B:
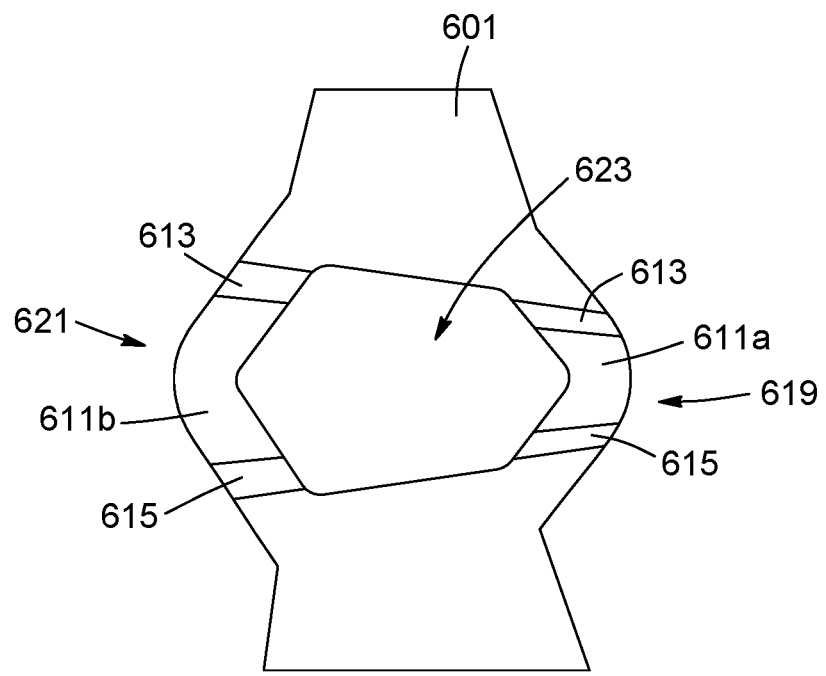
FIG. 6B is a rear view of the fixation plate of FIG. 6A.

With reference to FIGS. 1A and 1B, a fixation plate 600 is shown. Fixation plate 600 comprises a body 601 made from a rigid, biocompatible and degradation-resistant material, such as stainless steel or titanium, although it is appreciated that other materials are possible, including different metals and/or plastics and/or a combination thereof. In the present embodiment, fixation plate 600 is an osteotomy plate for securing to an antero-medial side of a patient's bone 3 and retaining an opening 7 formed therein during a high-tibial open-wedge osteotomy procedure. It is appreciated that in other embodiments, fixation plate 600 can be configured for securing to another side of the patient's bone 3 depending on surgical requirements. In the present embodiment, body 601 comprises a proximal section 601a for securing to the patient's bone 3 above opening 7, a distal section 601b for securing to the patient's bone 3 below opening 7, and an intermediate section 601c for spanning the opening 7. As will be described in more detail hereinafter, the present fixation plate 600 is patient-specific in that it has been designed based on the specific anatomy of the patient's bone 3 and based on the specific needs of the patient determined during a preoperative plan. The shape and configuration of fixation plate 600 can therefore vary from one procedure to another based upon the bone anatomy of different patients and based on their different needs.

The body 601 of fixation plate 600 is sized, shaped, and configured to fit snugly on the patient's bone 3 while also providing the required support and being minimally noticeable under the patient's skin. In the present embodiment, body 601 is thin and substantially flat, and is configured to follow the contours of the patient's bone 3. In this configuration, for example, when the fixation plate 600 is secured to the patient's bone 3, it can protrude from the surface of the patient's bone 3 at a uniform height along the entire body 601. Moreover, in some embodiments, body 601 can be designed to have a thickness which varies in different locations, allowing body 601 to have increased or reduced strength or rigidity where required and/or allow body 601 to protrude less noticeably from the patient's bone at certain areas.

The body 601 of fixation plate 600 comprises a bone interface side 603 and an outward-facing side 605. Bone interface side 603 comprises an inner surface for positioning adjacent the patient's bone 3. The contours of inner surface of bone interface side 603 are complementary in shape to surface contours of a predetermined position on the patient's bone 3. In this fashion, fixation plate 600 can fit snugly on a position of the patient's bone 3 determined preoperatively. Outward-facing side 605 is substantially smooth and/or flat to make it minimally noticeable under the patient's skin. In the present embodiment, the outward-facing side 605 comprises sloped and/or chamfered edges 607 which provide a smoother transition between the body 601 of fixation plate 600 and the patient's bone 3. The fixation plate 600 is secured to the patient's bone 3 via fasteners 609. In the present embodiment, fasteners 609 comprise surgical screws which are drilled into the patient's bone 3, although it is appreciated that other type of fasteners are possible. The fasteners 609 engage with plate 600 via apertures or canals 610 opening on the bone interface side 603 and the outward facing side 605 of the plate 600. As can be appreciated, canals 610 can be sized and shaped to receive different sizes of fasteners 609. Moreover, canals 610 can be configured to guide fastener 609 at a predetermined angle or orientation as it is inserted into the patient's bone 3. For example, in the present embodiment, canals 610 comprise sidewalls extending through the thickness of the body 601 of plate 600 at a predetermined angle to guide the fasteners 609 as they are drilled through the canals 610. In some embodiments, the sidewalls of canals 610 can be threaded, for example to engage with corresponding threads of fasteners 609 as the fasteners 609 are being drill through canals 610, and/or to engage or lock with a head of the fasteners 609 once fully inserted. The sidewalls of canals 610 can further be configured to abut against a head of fastener 609 to block the fastener 609 from being inserted too deep into the patient's bone 3.

As can be appreciated, based on a preoperative plan, fixation plate 600 can be designed with a different number and configuration of canals 610 for receiving a different number and configuration of fasteners 609 based on the specific needs of the patient to promote optimal securing of the plate 600. Moreover, the fixation plate 600 can be configured such that it can accommodate combinations of different sizes of fasteners 609 (both diameter and length) and different orientation of fasteners 609, for example based on the position of the patient's bone 3 to which a particular fastener 609 is to be secured. In the illustrated embodiment, the plate 600 is configured to accommodate two large laterally-spaced fasteners 609 in the proximal section of body 601a, and two smaller vertically-spaced fasteners 609 in the distal section of body 601b. As will be explained in more detail hereinafter, many other configurations of plate 600 are possible.

In some embodiments, additional support members can be provided to further assist fixation plate 600 in retaining the opening 7 formed in the patient's bone 3 and/or to assist in correctly positioning fixation plate 600 relative to opening 7. By way of example, and with reference to the embodiment of FIGS. 2, 2A, 2B, and 2C, a wedge element 611 can be provided to abut against internal surfaces 5a, 5b on opposite sides of opening 7 when fixation plate 600 is positioned on the patient's bone 3. As can be appreciated, as a load is applied across opening 7, the wedge element 611 can exert an opposing force on the patient's bone 3 via internal surfaces 5a, 5b. In this configuration, a load across the opening 7 can be borne by the wedge element 611 and dissipated through the patient's bone 3, rather than being borne by the fasteners 609 holding the plate 600 in place. In the illustrated embodiment, wedge element 611 is formed as an integral part of body 601 of fixation plate 600, and is made from the same rigid, biocompatible material, i.e. stainless steel or titanium. It is appreciated, however, that in other embodiments, wedge element 611 can be a separate piece which can be fastened or secured to the fixation plate 600 and/or directly to the patient's bone 3. It is further appreciated that wedge element 611 can be made of a different material, such as a rigid plastic or the like, depending on the required structural properties.

In the present embodiment, wedge element 611 extends from the bone interface side 603 of fixation plate 600, and is positioned on intermediate section 601*c* of fixation plate body 601. In this configuration, wedge element 611 extends inside opening 7 when the fixation plate 600 is secured to the patient's bone 3. The wedge element 611 comprises a proximal abutment 613 for abutting against a proximal internal surface 5*a* of bone 3, and a distal abutment 615 for abutting against a distal internal surface 5*b* of bone 3. Proximal 613 and distal 615 abutments are spaced apart from one another via a concave canal 617. In this configuration, a certain amount of flexure is permitted in the rigid body 601 of fixation plate 600 as a load is applied across abutments 613, 615. It is appreciated, however, that in other embodiments, wedge element 611 can be a solid block having abutments 613, 615 defined on opposite sides thereof.

As with the other components of fixation plate 600, the wedge element 611 can be configured according to patient-specific needs. For example, based on a preoperative plan and 3D models of the patient's bone 3, various components, surfaces, contours, etc. of the wedge element 611 and be shaped and configured to conform to the specific anatomy of the patient's bone 3 and/or opening 7 formed therein. Wedge element 611 can further be configured to provide varying levels of structural support as required based on patient-specific needs.

More specifically, and with reference to FIGS. 4 and 4A, an exemplary embodiment of a wedge element 611 is shown. In the illustrated embodiment, the body 601 of fixation plate 600 has a nominal thickness 602 in intermediate section 601*c*, and wedge element 611 extends therefrom. The wedge element 611 comprises proximal 613 and distal 615 abutments extending from body 601 and extends along a width 612*a* between anterior 619 and posterior 621 sides. The proximal 613 and distal 615 abutments have respective bone contacting bearing surfaces 613*a* and 615*a* spaced apart from one another by a spanning distance 612*b*, for respectively abutting against proximal 5*a* and distal 5*b* internal surfaces on opposite sides of opening 7 in the patient's bone 3. As can be appreciated, the spanning distance 612*b* can be adjusted according to the expected size of opening 7 as determined in a preoperative plan, to extend precisely between proximal 5*a* and distal 5*b* internal surfaces and abut against the same. By precisely spanning the distance between proximal 5*a* and distal 5*b* internal surfaces, wedge element 611 can provide the necessary support to retain the internal surfaces 5*a*, 5*b* a fixed distance from one another, and retain opening 7 at the desired opening angle. In this configuration, wedge element 611 can further assist in correctly positioning fixation plate 600 on the patient's bone 3. As can be appreciated, the wedge 611 will only be able to fit inside the opening 7 at a position where the opening is wide enough to accommodate the spanning distance 612*b* of abutments 613, 615. Accordingly, the wedge element 611 can be designed with a spanning distance 612*b* such that it fits inside opening 7 at a predetermined position and orientation relative to the patient's bone 3, as determined in a preoperative plan, thereby positioning the fixation plate 600 to which the wedge element 611 is secured.

Figure 12A:
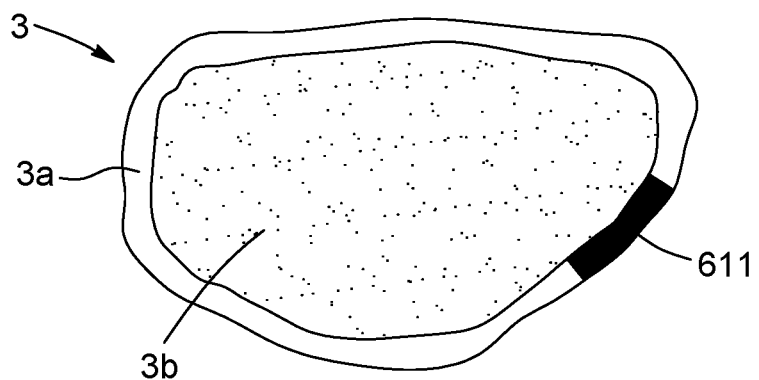
FIG. 12A is a cross sectional view showing a fixation plate secured to a patient's tibia bone, according to an embodiment in which the fixation plate is provided with a single wedge element conforming to the patient's cortical bone.

In the present embodiment, and as shown in FIG. 12A, wedge 611 is configured to abut against the patient's cortical bone 3*a*, i.e. the hard outer layer of patient's bone 3, as opposed to the soft trabecular bone 3*b*. Accordingly, and referring back to FIGS. 4 and 4A, proximal 613 and distal 615 abutments can be sized and shaped to interface with the patient's cortical bone 3*a* while avoiding contact with the patient's trabecular bone 3*b*. More particularly, in the present embodiment, bone contacting surfaces 613*a* and 615*a* are substantially planar and extend substantially perpendicular relative to body 601 through respective depths 614*a* and 616*a*. As can be appreciated, depths 614*a* and 616*a* can be adjusted based on the thickness of the patient's cortical bone 3*a*, such that the abutments 613 and 615 extend into opening 7 to a depth corresponding to the thickness of the cortical bone 3*a*, for example to approximately 4 mm. In the present embodiment, bone contacting surfaces 613*a* and 615*a* have the same depths 614*a*, 616*a*, but it is appreciated that in other embodiments, the depths can be different, for example depending on the expected position and orientation of wedge 611, and/or variances in the thickness of the patient's cortical bone 3*a*. As can be appreciated, the surface areas of bearing surfaces 613*a* and 615*a* are defined by depths 614*a*, 616*a*, and width 612*a* of wedge 611. Accordingly, width 612*a* can be adjusted, in addition to depths 614*a*, 616*a*, according to the required surface area of bearing surfaces 613*a*, 615*a*. In the present embodiments, width 612*a* is approximately 8 mm, but other sizes are also possible depending on patient-specific requirements.

As mentioned above, the wedge element 611 can be configured to provide different levels of support based on patient-specific needs. For example, for some patients, it may be desirable to have more rigidity in the fixation plate 600, whereas for other patients, it may be desirable to allow a certain amount of micromovements via flexure or deformation of the fixation plate 600 across the opening 7. Accordingly, respective thicknesses 614*b* and 616*b* of proximal 613 and distal 615 abutments can be adjusted based on a desired level of rigidity. For example, in some embodiments, such as the one illustrated in FIGS. 4 and 4A, abutments 613, 615 can be relatively thin members extending from body (for example with thicknesses 614*b* and 616*b* of approximately 1 mm), thus allowing a certain amount of deformation as loads are applied to their respective bearing surfaces 613*a*, 615*b*. In other embodiments, abutments 613, 615 can be relatively thick and/or can have a thickness corresponding to the spanning distance 612*b* of wedge 611 (i.e. the wedge being formed from a solid block of material, with abutments 613, 615 defined on opposite sides thereof), thereby providing increased rigidity and allowing little to no deformation of wedge 611 under typical loads. In the embodiment illustrated in FIGS. 4 and 4A, the respective thicknesses 614*b*, 616*b* of abutments 613 and 615 are the same, however it is appreciated that in other embodiments they can be different, for example to provide different levels of rigidity in proximal and distal sections of plate 600 and/or to control the distribution of forces in wedge 611 as a load is applied to abutments 613, 615.

As can be appreciated, abutments 613 and 615 can be designed with different shapes and configurations which can further affect the rigidity and/or the distribution of forces in wedge 611. For example, in the embodiment shown in FIGS. 4 and 4A, abutments 613 and 615 are configured as curved members with a progressive reduction of their depths 614*a*, 616*a* towards a central area of wedge 611. In other words, a canal 617 extends along a height 617*a* between respective interior edges 613*b*, 615*b* of abutments 613 and 615. The canal 617 has a depth 617*b* which increases towards the central area of wedge 611, thereby subtracting from the depths of abutments 613, 615. In the present embodiment, the depth 617*a* of canal 617 follows a polynomial curve (i.e.

$AX^2+BX+C$), reaching a maximum depth 617b midway along its height 617a. Thus, when viewed from posterior 219 or anterior 221 sides, the canal 617 has a parabolic or C-shaped profile. In this configuration, when a load is applied across abutments 613, 615, stresses can be focused towards the central area of the wedge 611. Although in the present embodiment the canal 617 is substantially C-shaped, it is appreciated that other configurations are also possible, including different shapes having progressive and/or abrupt changes in depth 617b. For example, in some embodiments, the canal 617 can have a substantially V-shaped profile, a substantially rectangular-shaped profile, etc. In the present embodiment the maximum depth 617a of canal 617 corresponds to the depths 614a, 616a of abutments 613, 615. In this configuration, the canal 617 does not extend past the thickness 602 of plate 600. It is appreciated, however, that other configurations are possible. For example, the canal 617 can be shallower than depths 614a, 616a, such that a minimum or base thickness 618 of plate 600 between abutments 613, 615 is thicker than a nominal thickness 602 of plate 600 adjacent to the wedge 611.

In the illustrated embodiment, the wedge 611 can be referred to as a straight wedge in that the bearing surfaces 613a, 615a are substantially straight and uniform. For example, bearing surfaces 613a, 615a are substantially rectangular, and are substantially parallel to one another. Similarly, the canal 617 is straight and uniform along the width 612a of wedge 611. It is appreciated, however, that the shape and orientation of bearing surfaces 613a, 615a, and/or canal 617 can be adjusted to better conform to the specific needs of a patient. For example, as illustrated in FIGS. 8, 8A and 8B the surface area of bearing surfaces 613a, 615a of a straight wedge 611 may not be in full contact with interior surfaces 5a, 5b of opening 7, and can thus create areas of increased pressure. However, if wedge 611 is configured to follow the shape of interior surfaces 5a, 5b as shown in FIGS. 9, 9A and 9B, a superior interface between wedge 611 and the patient's bone 3 can be achieved (i.e. increased surface area of contact), allowing for better stress distribution through the bone.

Figure 10:
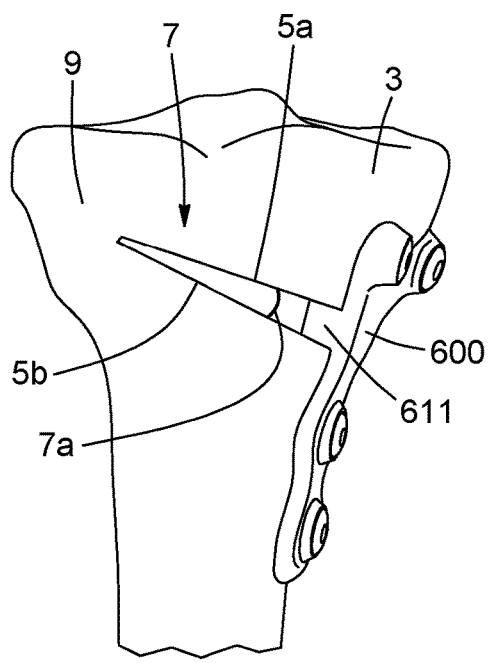
FIG. 10 is a side perspective view of an open wedge formed in a patient's tibia bone supported by a fixation plate with a bone conforming wedge having tapered bearing surfaces, according to an embodiment.
Figure 10A:
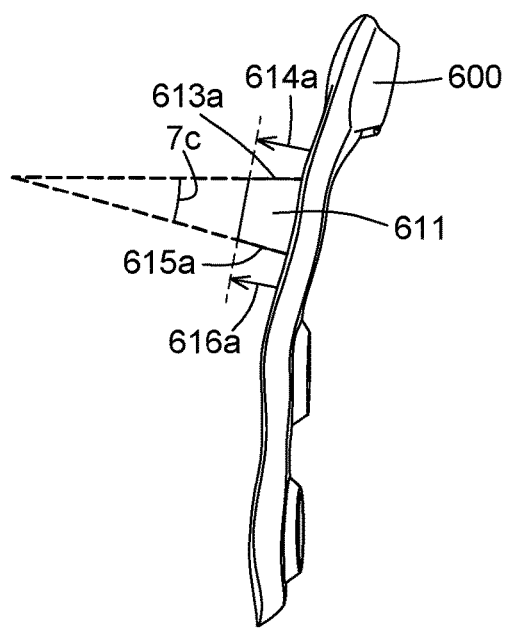
FIG. 10A is a side view of the fixation plate of FIG. 10.

With reference now to FIGS. 3, 3A and 3B, a wedge element 611 is shown according to an alternate embodiment in which abutments 613, 615 are shaped to follow the specific shape and contours of opening 7. More specifically, in the illustrated embodiment, bearing surfaces 613a, 615a are sloped or tapered along the direction of width 612a. Similarly, bearing surfaces 613a, 615b are sloped or tapered along the direction of their depths 614a, 616a. In this configuration, when the wedge 611 is positioned inside opening 7, bearing surfaces 613a, 615a can follow the slope of interior surfaces 5a, 5b, and increase the contact surface area therewith. This configuration of wedge 611 can further allow for the correction of *varus*/valgus deformity in the frontal plane as well as the correction of the tibial slope in the sagittal plane. In the present embodiment, bearing surfaces 613a, 615b are tapered inwards along width 612a towards the posterior side 621, to follow a corresponding narrowing of opening 7 towards a posterior side of the patient's bone 3. It is appreciated, however, that the tapering direction and magnitude can differ according to the expected shape of the opening 7 as determined in a preoperative plan. It is also appreciated that the proximal 613a and distal 615a bearing surfaces can be tapered at different angles. In the present embodiment, bearing surfaces 613a, 615a are also tapered inward along the direction of their depths 614a, 616a. In this configuration, the bearing surfaces 613a, 615a can follow the slope of interior surfaces 5a, 5b as they converge towards hinge 9 at opening angle 7a, as shown in FIGS. 10 and 10A. Again, it is appreciated that the tapering angle of bearing surfaces 613a, 615a can be different.

Figure 11:
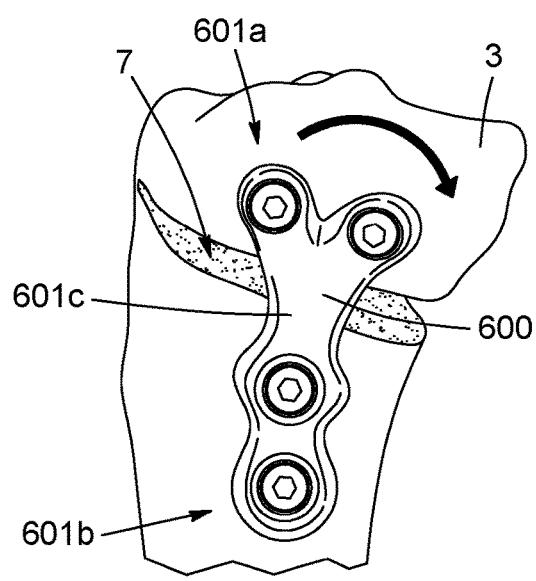
FIG. 11 is a front perspective view of an open wedge formed in a patient's tibia bone supported by a fixation plate with a bone confirming wedge having offset bearing surfaces, according to an embodiment.
Figure 11A:
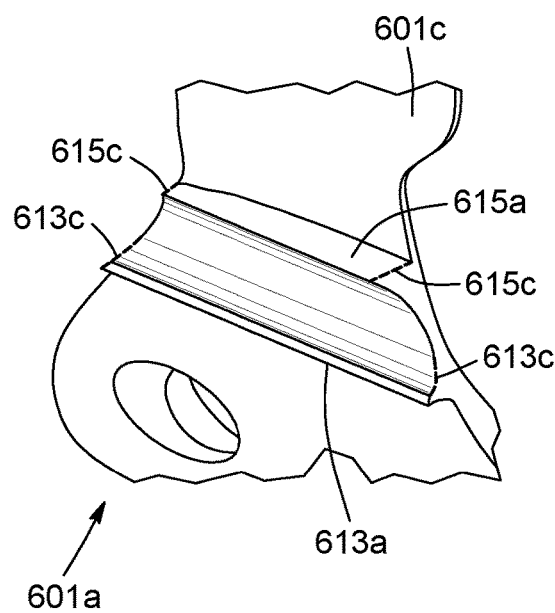
FIG. 11A is a detail view of the wedge element of the fixation plate of FIG. 11.

In the present embodiment, the width 612a of the wedge 611 is uniform along the wedge span 612b. In other words, bearing surfaces 613a, 615a are aligned with one another, and have the same width 612a. It is appreciated, however, that in other embodiments, bearing surfaces 613a, 615a can have different widths and/or can be offset from one another. For example, as illustrated in FIGS. 11 and 11A, load distribution in the patient's bone 3 can be physiologically more important in the medial compartment. Accordingly, when plate is secured to patient's bone 3 across opening 7, the plate 600 can undergo a rotation effort in the antero-medial plane. To equilibrate the stress induced in the wedge 611 and bone 3, bearing surfaces 613a, 615a can have different widths and/or can be offset, for example by being configured with tapered side edges 613c, 615c. It is appreciated that other relative size and positions of bearing surfaces 613a, 615a are also possible in different embodiments, according to patent specific requirements.

In the embodiment illustrated in FIGS. 3, 3A and 3B, the wedge element 611 is further configured with bearing surfaces 613a, 615a which conform to a shape of the patient's cortical bone 3a to ensure better contact therewith, and avoid contact with the trabecular bone 3b. As can be appreciated, the thickness of the patient's cortical bone 3a can vary at different points along the circumference of the patient's bone 3. Accordingly, the respective depths 614a, 616a of abutments 613, 615 can in direction of wedge width 612a. In the present embodiment, and as best illustrated in FIG. 3B, depths 614a of proximal abutment 613 decreases from anterior side 619 to posterior side 621, thus defining a bearing surface 613a having a sloped or tapered interior edge shaped to match a thinning of the patient's cortical bone 3a towards posterior side 621. Although in the present embodiment the interior edge of bearing surface 613a has a sloped, linear shape, it is appreciated that other shapes are also possible depending on the specific shape of the patient's cortical bone 3a. Moreover, although only the proximal abutment 613 is shown in FIG. 3B, it is appreciated that distal bearing surface 615a can be configured with a similar or different shape.

In the present embodiment, the wedge element 611 is further configured with an evolutive canal 617, i.e. a canal having a shape which changes or evolves along width 612a of wedge 611. As shown in FIGS. 3, 3A and 3B, the height 617a of canal 617 varies along width 612a wedge. More specifically, interior edges 613b, 615b of abutments 613, 615 are tapered inwards from posterior side 621 to anterior side 619, resulting in the canal height 617a decreasing from posterior side 621 to anterior side 619. In the present embodiment, edges 613b, 615b are angled inward towards one another at substantially equal and opposite angles, although it is appreciated that in other embodiments, angles of edges 613b, 615b can differ, or edges 613b, 615b can be angled and parallel to one another. It is further appreciated that in other embodiments, edges 613b, 615b can follow curved paths. As can be appreciated, the present configuration of canal 617 can also allow abutments 613, 615 to have evolutive thicknesses 614b, 616b along width 612a. More particularly, in the present embodiment, respective thicknesses 614b, 616b of abutments 613, 615 increase from posterior side 621 to anterior side 619.

In the present embodiment, the wedge element 611 is further configured with a minimum or base thickness 618 of plate 600 which varies along width 612a of wedge 611. As best shown in FIG. 3B, the base thickness 618 increases from posterior side 621 to anterior side 619. For example, on posterior side 621, the base thickness 618 can correspond to the nominal thickness 602 of plate 600, whereas on anterior side 619, the base thickness 618 can be greater than the nominal thickness 602. Although in the present embodiment the base thickness 618 increases linearly along width 612a, it is appreciated that in other embodiments, the change in thickness 618 can be nonlinear. As can be appreciated, variances in base thickness, along with the variances in the canal configuration and/or abutment thicknesses can allow for the rigidity and/or permitted amount of micromovements between abutments 613, 615 to vary across the width 612a of wedge 611.

In the embodiments described above, plate 600 is provided with a single wedge 611 was shown for engaging in opening 7 along an antero-medial side of the patient's bone 3. It is appreciated, however, that in other embodiments, other wedge configurations are possible. For example, with reference to FIGS. 5, 5A, 5B, 6A and 6B, a double wedge plate 600 is shown according to an embodiment. In the illustrated embodiment, plate 600 is provided with a first anterior wedge 611a, and a second posterior wedge 611b spaced apart from one another in intermediate section 601 of plate body 601. In the present configuration, wedges 611a and 611b are spaced apart from one another via an opening 623 in plate body 601. As can be appreciated, opening 623 can help reduce the weight of plate and/or to encourage flexure in the intermediate section 601c. It is appreciated that in other embodiments, opening 623 need not be provided, and plate body 601 can be closed between wedges 611a and 611b.

Figure 12B:
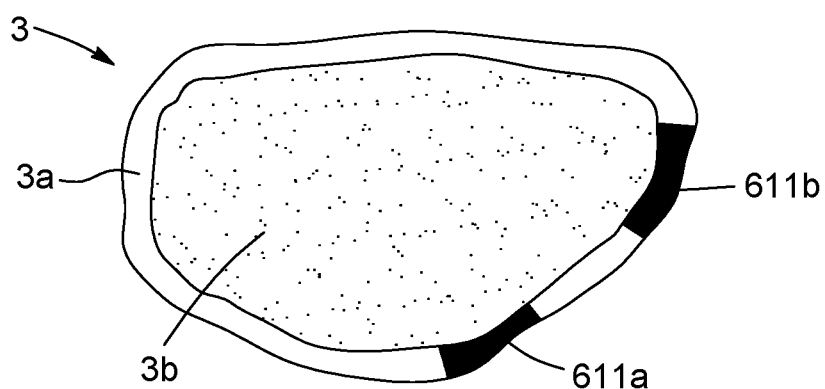
FIG. 12B is a cross sectional view showing a fixation plate secured to a patient's tibia bone, according to an embodiment in which the fixation plate is provided with two wedge elements conforming to the patient's cortical bone.

When plate 600 is engaged with patient's bone 3, wedges 611a and 611b engage in opening 7 on an antero-medial side of the patient's bone 3, providing support at anterior and posterior positions. As with the embodiments of the patient-specific wedges described above, each of wedges 611a and 611b can be configured according to patient-specific needs, and based on patient-specific anatomy. For example, as illustrated in FIG. 12B, each of wedges 611a and 611b can be shaped and configured to follow and abut the patient's cortical bone 3a. The other size and shape parameters of wedges 611a and 611b, as described above, can also be customized based on the expected position of wedge 611a, 611b as determined preoperatively, and the dimensions of wedges 611a, 611b can differ from one another. For example, in the present embodiment, posterior wedge 611b has a spanning distance greater than the spanning distance of anterior wedge 611a to account for a widening of opening 7 towards the posterior. The size, shape and configuration of wedges 611a, 611b can further be configured such that wedges 611a and 611b work together to provide the necessary level of support, and/or account for stress distribution in the plate 600 and/or the patient's bone 3 based on patient-specific requirements as determined preoperatively.

Figure 7:
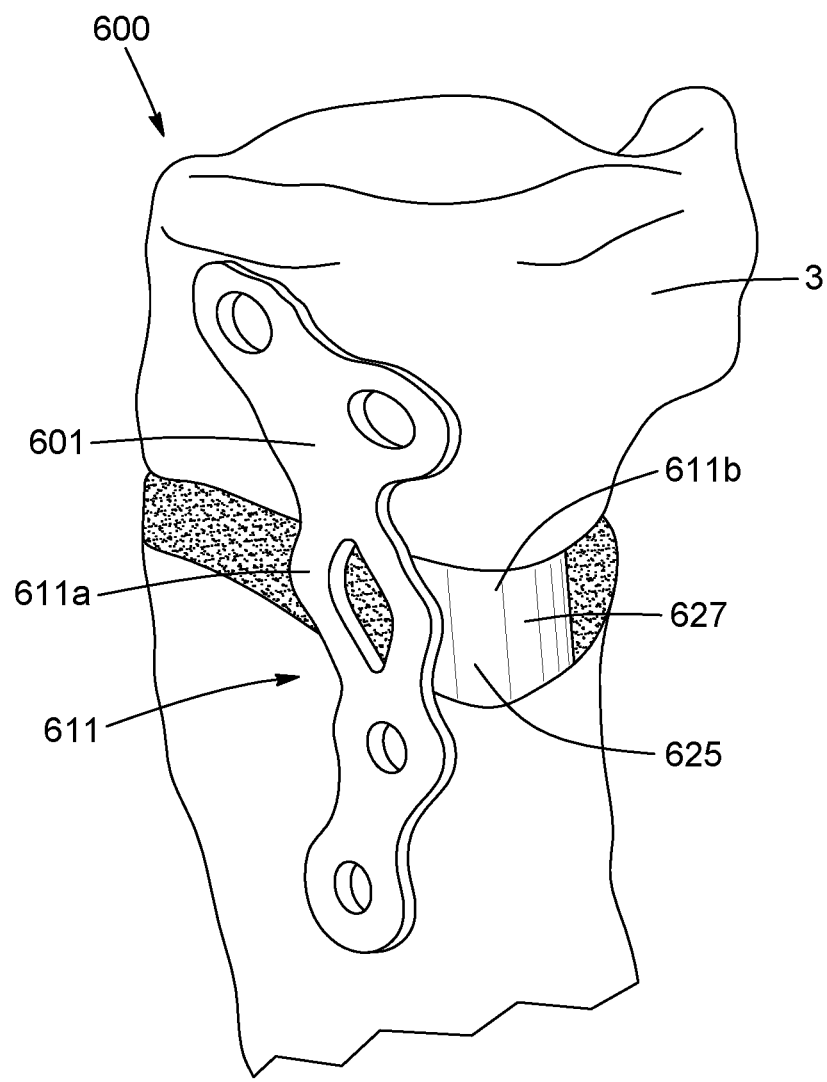
FIG. 7 is a perspective view of a fixation plate securing an open wedge formed in a patient's tibia bone, according to an embodiment in which the fixation plate is provided with a C-shaped wedge element.
Figure 12C:
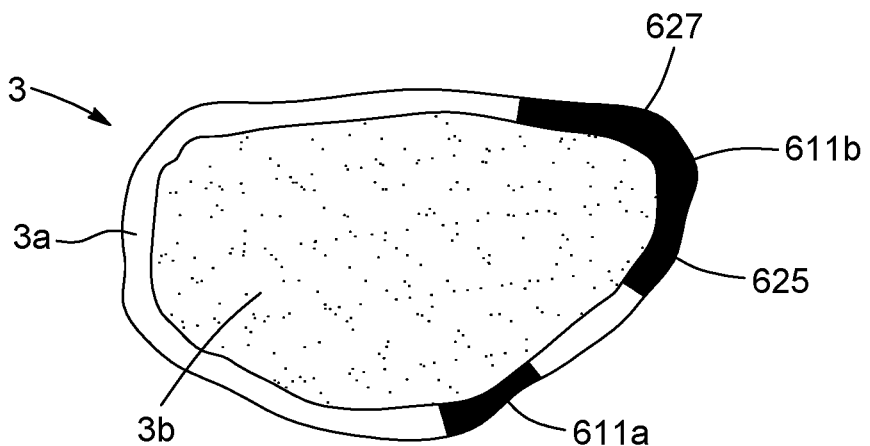
FIG. 12C is a cross sectional view showing a fixation plate secured to a patient's tibia bone, according to an embodiment in which the fixation plate is provided with C-shaped wedge element conforming to the patient's cortical bone.

In the embodiments described above, the wedge 611 is configured to engage in, and provide support to, opening 7 on an antero-medial side of the patient's bone 3. It is appreciated, however, that in some embodiments, further support may be desired towards the anterior and/or posterior of the patient's bone 3. Accordingly, in some embodiments, the wedge 611 can be configured as an extended wedge with a section which extends away from the plate body 601 in the anterior and/or posterior direction. With reference to FIG. 7, an exemplary fixation plate 600 with an extended wedge 611 is provided. In the illustrated embodiment, the wedge 611 is a double wedge and comprises an anterior wedge element 611a and a posterior wedge element 611b. The posterior wedge element 611b is configured as an extended wedge which comprises an anterior section 625 extending from plate body 601 along the antero-medial section of the patient's bone 3, and a posterior section 627 which extends from anterior section 625 towards the posterior of the patient's bone 3. As can be appreciated, and as shown in FIG. 12C, the extended wedge element 611b is configured to follow the contour of the patient's bone 3 as it wraps around towards the posterior, and therefore defines a C-shape. It is appreciated, however, that other shapes are possible. It is further appreciated that in other embodiments, the extended wedge can comprise an anterior-extending section which can wrap around an anterior surface of the bone. It should be appreciated that although the posterior wedge 611b is configured as an extended wedge in the present embodiment, in other embodiments the anterior wedge 611a can be configured as an extended wedge in place of, or in addition to the posterior wedge 611b. Finally, it should be appreciated that an extended wedge can be provided as part of a plate having a single wedge.

As can be appreciated, as with the other embodiments of wedges describes above, the extended wedge 611 can have contours and surfaces that conform to the specific shape of the patient's bone 3. For example, as shown in FIG. 12C, the extended wedge 611b can be sized and shaped to follow and abut against the patient's cortical bone 3a, while avoiding the trabecular bone 3b. The extended wedge 611b can further be configured with tapered and/or offset abutments surfaces as described above and can be provided with a straight or evolutive channel to provide flexure if desired.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A fixation plate for securing an opening formed in a bone, the fixation plate comprising:
   a body securable to the bone, the body having an anterior side, a posterior side, a bone interface side and an outward facing side; and
   a wedge element of unitary construction with the body, the wedge element extending from the bone interface side of the body for inserting into the opening formed in the bone, the wedge element having a proximal abutment with a proximal bone contacting bearing surface for abutting against a proximal internal surface of the bone in the opening and a distal abutment with a distal bone contacting bearing surface for abutting against a distal internal surface of the bone in the opening,
   each one of the proximal bone abutment and the distal abutment extending along a width direction between the anterior side and the posterior side of the body and a depth direction,
   the distal abutment being spaced-apart from the proximal abutment by an evolutive canal;
   wherein the wedge element is patient-specific and the proximal and the distal bone contacting bearing surfaces are shaped to conform to contours of the opening formed in the bone, the evolutive canal having a shape which tapers in at least one of the width direction, between the anterior side and the posterior side of the body, and the depth direction, between the bone interface side and free ends of the distal and proximal abutments, based at least in part on the wedge element conforming to the contours of the opening formed in the bone.

2. The fixation plate according to claim 1, wherein the proximal bone contacting bearing surface and the distal bone contacting bearing surface are sized to abut against cortical sections of the proximal and distal internal surfaces of the bone.

3. The fixation plate according to claim 1, wherein the evolutive canal between the proximal abutment and the distal abutment tapers in the width direction.

4. The fixation plate according to claim 1, wherein the evolutive canal between the proximal abutment and the distal abutment tapers in the depth direction.

5. The fixation plate according to claim 1, wherein each one of the proximal and distal abutments extends between an anterior side edge and a posterior side edge, further wherein at least one of the anterior and posterior side edges is tapered along the depth direction.

6. The fixation plate according to claim 1, wherein the proximal and the distal bone contacting bearing surfaces have respective surface areas which are different from one another.

7. The fixation plate according to claim 1, wherein the proximal and the distal bone contacting bearing surfaces are not in register with one another.

8. The fixation plate according to claim 1, wherein the evolutive canal is shaped with a curved depth profile.

9. The fixation plate according to claim 1, wherein the wedge element comprises an anterior section extending from the posterior side of the body along a width, and a posterior section extending from the anterior section along a width.

10. The fixation plate according to claim 9, wherein the anterior and posterior sections of the wedge element together define an extended wedge element having a curved profile following a contour of the bone.

11. The fixation plate according to claim 10, wherein the extended wedge element is shaped to extend along at least a first face of the bone, and a second face of the bone posterior to the first face.

* * * * *